United States Patent [19]
Vartanian

[11] Patent Number: 6,163,589
[45] Date of Patent: Dec. 19, 2000

[54] MONTE CARLO SCATTER CORRECTION METHOD FOR COMPUTED TOMOGRAPHY OF GENERAL OBJECT GEOMETRIES

[75] Inventor: Michael H. Vartanian, San Jose, Calif.

[73] Assignee: General Electric Company, Schenectady, N.Y.

[21] Appl. No.: 09/097,047

[22] Filed: Jun. 13, 1998

[51] Int. Cl.[7] ................................................. G01N 23/083

[52] U.S. Cl. .................................. 378/7; 378/4; 378/901; 382/131

[58] Field of Search ................................ 378/4, 7, 8, 15, 378/901; 382/131

[56] References Cited

U.S. PATENT DOCUMENTS 5,905,809  5/1999  Timmer ..................................... 382/131

Primary Examiner—David Vernon Bruce

[57] ABSTRACT

A method of correcting aberrations caused by target x-ray scatter in three-dimensional images generated by a volumetric computed tomographic system is disclosed. The method uses a Monte Carlo simulation to determine the distribution of scattered radiation reaching the detector plane. The geometry for the scatter calculation is determined using the uncorrected three-dimensional tomographic image. The calculated scatter is used to correct the primary projection data which is then processed routinely to provide the corrected image.

1 Claim, 5 Drawing Sheets http://ehssun.lbl.gov/egs/epub.html

EGS Manuals and Documentation

The EGS4 code system is documented in *The EGS4 Code System*, by W.R. Nelson, H. Hirayama, and D.W.O. Rogers, SLAC-265 (1985). To obtain a printed copy of the EGS4 manual, write to W. Ralph Nelson at Stanford Linear Accelerator Center P.O. Box 4349

Stanford, CA 94309 and ask for SLAC-265. Be sure to include a brief description of what you plan to do with EGS.

For your convenience, SLAC-265 appendices 2 through 5 have been converted to HTML and made accessible here.

- SLAC-265 Appendix 2: EGS4 User Manual in HTML. (61 kb)
- SLAC-265 Appendix 3: PEGS4 User Manual in HTML.(78 kb)
- SLAC-265 Appendix 4: EGS4 User Guide to Mortran3 in HTML.(36 kb)
- SLAC-265 Appendix 5: EGS4 System Considerations in HTML. A bit dated, but you may still find it useful.(26 kb)

Links to a few more EGS related documents are provided below. Since these files are fairly large, please download them during off hours (i.e., from 6 pm to 8 am PST). Additional EGS

FIG. 3 information and documents can be found on the NRC Ionizing Radiation Standards group (Canada) web page.

Mortran

- *Advanced Mortran3*

W Ralph Nelson. ps (176 kb) or pdf (145 kb)

- *Elementary Mortran3*

W Ralph Nelson. ps (145 kb) or pdf (120 kb)

History, Installation, and Use

- *EGS4 in '94 A Decade of Enhancements*

W.R. Nelson, A.F. Bielajew, D.W.O. Rogers, and H. Hirayama ps (1926 kb) or pdf (298 kb)

- *History, overview and recent improvements of EGS4*

A.F. Bielajew, H. Hirayama, W.R. Nelson, and D.W.O. Rogers. ps (306 kb) or pdf (295 kb)

- *HOWFAR -- How to code geometry*

W Ralph Nelson. ps (2188 kb) or pdf (337 kb)

- *HOWFAR and HOWNEAR: Geometry Modeling for Monte Carlo Particle Transport*

Alex F Bielajew. pdf (565 kb)

- *How to manage the EGS4 system*

Alex F Bielajew. ps (193 kb) or pdf (178 kb)

- *Running EGS4 on other machines*

FIG. 3

Alex F Bielajew. ps (386 kb) or pdf (319 kb)

PEGS4 (cross sections)

- *PEGS4--Data sets for different media*
    W Ralph Nelson. ps (593 kb) or pdf (212 kb)

Other

- *Efficiency statistics and sampling*
    Alex F Bielajew ps (216 kb) or pdf (209 kb)

- *Electron Monte Carlo simulation*
    Alex F Bielajew and W Ralph Nelson. ps (379 kb) or pdf (236 kb)

- *Graphics!*
    Alex F Bielajew ps (97 kb) or pdf (108 kb)

- *Monte Carlo Modeling in External Electron-Beam Radiotherapy: Why Leave It to Chance?*
    Alex F Bielajew ps (2156 kb) or pdf (318 kb)

- *Photon Monte Carlo simulation*
    Alex F Bielajew. ps (288 kb) or pdf (197 kb)

- *Variance reduction techniques*
    Alex F Bielajew and W Ralph Nelson. ps (236 kb) or pdf (232 kb)

FIG. 3

MONTE CARLO SCATTER CORRECTION METHOD FOR COMPUTED TOMOGRAPHY OF GENERAL OBJECT GEOMETRIES

CROSS-REFERENCE TO RELATED APPLICATIONS

This application claims the benefit of the earlier filing date of provisional application Ser. No. 60/050,064 filed Jun. 14, 1997.

STATEMENT REGARDING FEDERALLY SPONSORED RESEARCH OR DEVELOPMENT

Not applicable

REFERENCE TO A MICROFICHE APPENDIX

Not applicable

BACKGROUND

1. Field of Invention

This invention relates to the correction of image aberrations caused by x-ray scatter when performing volumetric computed tomography of industrial machine parts.

2. Description of Prior Art

Scatter is a deflection in x-ray direction caused by certain interactions within the target material. This can create a background which corrupts the directly transmitted signal of interest (FIG. 1). The phenomenon is significant in computed tomography of industrial machine parts because metals scatter x-rays to a greater degree, and is especially deleterious for three-dimensional, volumetric computed tomography where the entire object is irradiated by a cone beam of x-rays. This spatially-varying background adds to the true signal and can produce pronounced artifacts when the three-dimensional image of the object is mathematically reconstructed.

The primary measurement data in volumetric computed tomography are sets of two-dimensional x-ray projections taken from various angles with respect to the object. In what follows, it is assumed that a complete volumetric computed tomographic system is available, that the distribution of x-ray intensity in the various projection views has been detected, measured, and digitized in some manner known to the art, and that these two-dimensional arrays of numbers representing the various projection views are accessible for numerical operation by the computer. It is further assumed that the projection arrays are afterwards combined and processed according to the known methods of volumetric computed tomography to produce a three-dimensional density map, or image, of the object.

It is known that the image artifacts caused by scattered x-rays falling on the various projection views can be corrected if the fraction of total signal at each point of every projection caused by scatter is estimated and then digitally subtracted before the projections are combined in the image reconstruction step (FIG. 2).

Until now, the main approach for estimating this scattered component has been by making ancillary measurements using a series of x-ray blocking slits of varying width placed between the object and the x-ray detector. The rationale is that the scattered signal, being incident from a range of directions, can be estimated by extrapolating the series of slit measurements to zero width. However, such a method requires extensive added hardware and provides only a coarse grid of scatter estimates. More importantly, this approach has proven experimentally difficult and unable to provide accurate scatter estimates.

A different approach has involved calculation of the scattered signal from physical first principles using prior knowledge of the object geometry. Accurate scatter estimates are possible in this way using Monte Carlo radiation transport computer codes. However such calculations have hitherto been limited to very simple object forms by the apparent requirement, dictated by universal practice, that the geometry be specified using the standard formulae of three-dimensional coordinate geometry. The fact that such formulae require extensive algebraic manipulation to cast them in a form suitable for digital computation has made this approach prohibitive for all but the simplest models. For this reason, the Monte Carlo method has not until now appeared useful for application to the computed tomography of actual industrial parts.

BRIEF SUMMARY OF THE INVENTION

The invention extends the Monte Carlo scatter correction method to arbitrary object geometries. In place of analytical formulae, the geometry is defined using the uncorrected, three-dimensional tomographic image. On this basis, the x-ray scatter can be accurately calculated and used to correct the image as previously described.

BRIEF DESCRIPTION OF THE DRAWINGS

FIG. 3 shows information for the EGS4 Monte Carlo Code System.

DETAILED DESCRIPTION OF THE INVENTION

Figure 1:
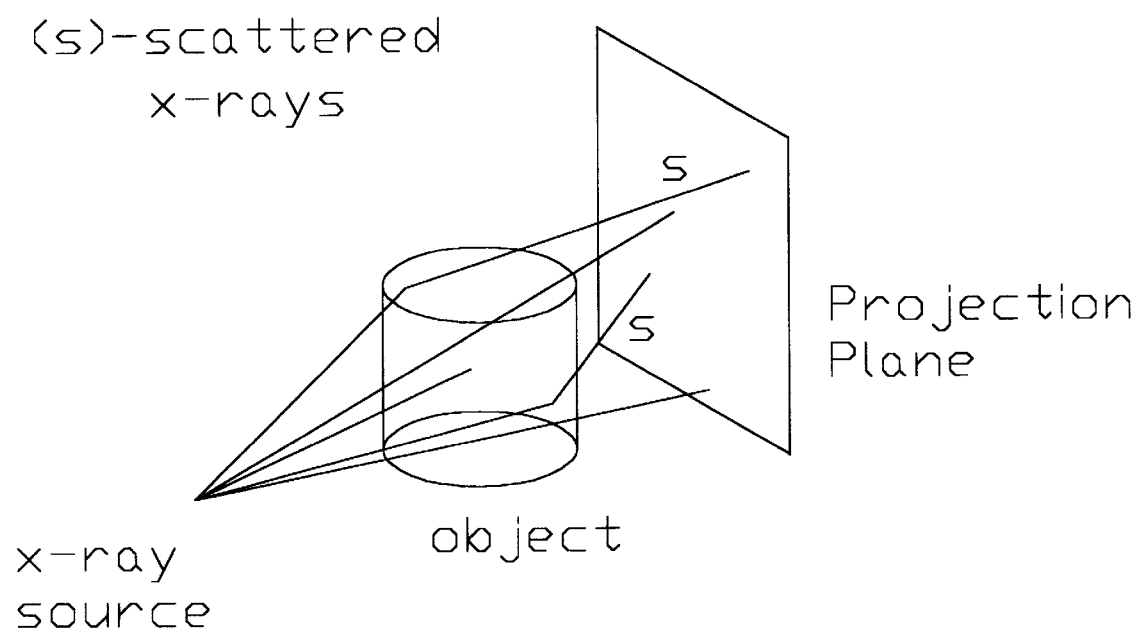
FIG. 1 shows scattered x-ray background corrupting a projection view measurement.
Figure 2:
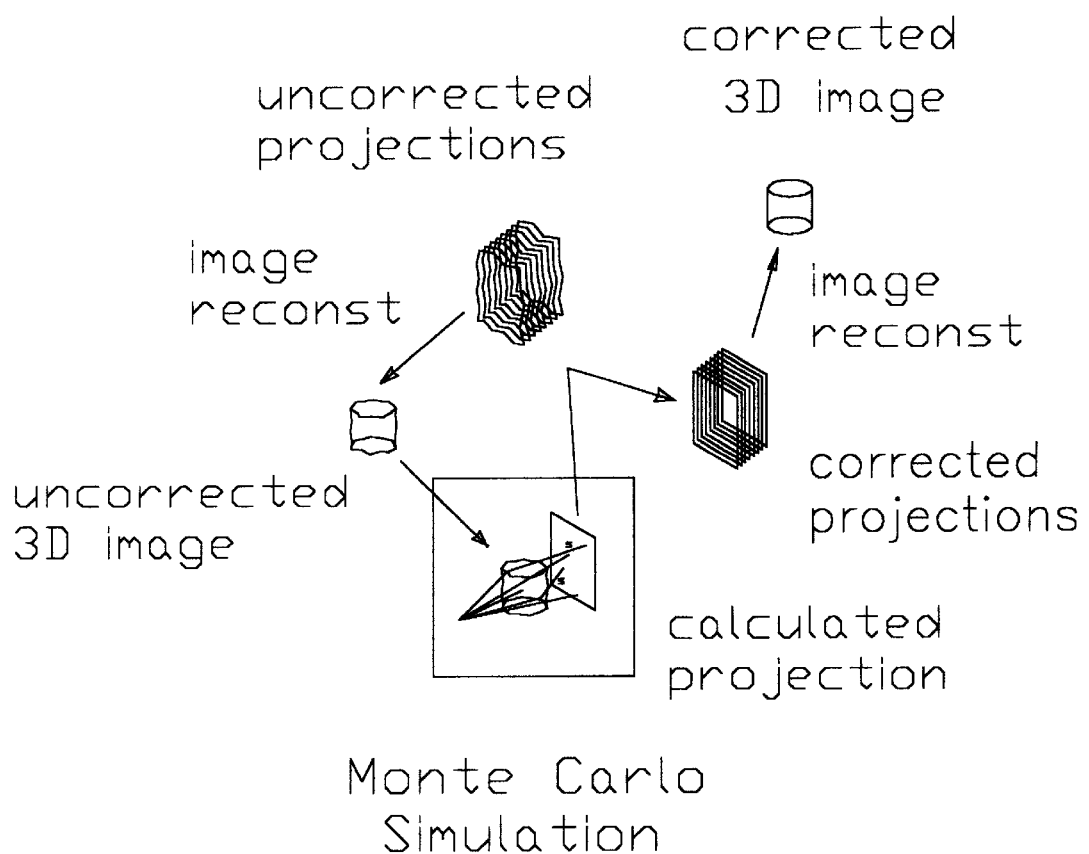
FIG. 2 shows the process for scatter correction.

The preferred embodiment of the invention uses the Monte Carlo computer code named ELECTRON-GAMMA SHOWER Version 4 ("EGS4 Code System"). The EGS4 Code System was developed at the Stanford Linear Accelerator Center under the sponsorship of the United States Department of Energy and resides in the public domain.

The EGS4 Code System includes extensive tutorial information which will enable a person skilled in the art to make and use the invention (FIG. 3). In particular, the information teaches how to set up a spatial coordinate system in the EGS4 code to simulate the volume of space occupied by the source of x-rays and the planar section corresponding to the x-ray detector which generates the projection views. The simulated projection plane is partitioned into a two-dimensional array of picture elements corresponding to that of the measured projection views.

The EGS4 Code System is a package of subprograms which calculates, among other things, the fundamental interactions of x-rays with matter. Monte Carlo codes are used for calculations with complicated geometries in a wide variety of general physics applications. These codes adopt a quantum mechanical picture in which the x-rays, or the penetrating radiation in general, propagate freely along straight rays and interact at points with localized atoms. The subroutines calculate the probability distributions of various interactions, in particular the scattering of x-rays by atoms into different directions. An individual x-ray propagates, or is transported, through the geometry, its various random interactions being determined by sampling the probability distributions with computer generated random numbers. The overall features of x-ray interaction with the target, including the amount of scattered signal reaching a given point on a projection view, are then found as the statistical average of a large number of individual x-ray histories.

The EGS4 documentation teaches how to track these individual histories, how to tag the x-rays that undergo scattering interactions, and how to count the scattered x-rays which reach a given point on the projection plane and are subsequently detected. A person skilled in the art will furthermore be able to scale this simulated number of detected, scattered x-rays into a number commensurate with the two-dimensional arrays of numbers representing the actual projection views measured by the volumetric computed tomographic system and made available for numerical operation as previously assumed.

Among the two or three Monte Carlo codes in general use, the EGS4 Code System is advantageous for realizing the invention described herein. This is due to its flexibility as to how x-ray transport through the object is controlled. Because of this, it is only necessary to discuss one user-written subroutine named HOWFAR, the general purpose of which is fully described in the documentation accompanying the EGS4 Code System. The remainder of the EGS4 Code System operates normally.

The function of HOWFAR is to determine the distance from a given point inside the object to its surface boundary along a given direction. The three spatial coordinates of the given point and the three cosines of the given direction are input to HOWFAR. The subroutine returns distance to the surface. This quantity is basic to the transport process because it determines the probability that an x-ray starting at the given point will interact with an atom along the given direction before escaping the object. The x-ray transport through the object, and the scattered radation which finally calculated, is entirely determined by this distance quantity returned on successive calls to HOWFAR.

Until now, the distance returned by HOWFAR has been computed in terms of complicated algebraic rearrangements of the analytical equations describing the particular object surface under study. Extensive logic must also be encoded to select the appropriate surface when the boundary is formed from several intersecting surfaces as is typically the case. Such approaches have been universal practice for Monte Carlo codes in one way or another, and has made the method impractical for application to complicated geometries, in particular industrial machine parts.

However, the fact that this particular application of the Monte Carlo code involves three-dimensional images obtained by volumetric computed tomography opens up a new way to determine the distance calculated by HOWFAR. The invention utilizes the uncorrected image of the object available from the computed tomographic system to determine the required distance calculated by HOWFAR. In this way the scatter calculations can be carried out without prior knowledge or characterization of the object geometry.

Because the geometry is determined using the aberrated image, the effect of artifacts on the accuracy of the scatter calculation is considered. Since the invention is specifically applied to the tomography of metallic parts, the object density is known to be spatially uniform, notwithstanding any aberrations present. This allows the position of the boundary surface to be accurately determined using the method described below. Furthermore, the distribution of scattered radiation emanating from the target depends primarily on the bulk material distribution rather than the boundary. For these reasons, the overall method is robust and requires little experimentation to develop or intervention in actual operation. The corrected three-dimensional image may also be used in an iterative fashion to better determine the scattered x-rays. However, convergence to a final result will in most cases be accomplished in a single pass.

The image generated by the volumetric computed tomographic system is assumed available as a three-dimensional array of numbers where positive values correspond to the material object and zero values to empty space. This array of volume elements ("voxels") can be imported into the computer memory allocated to the Monte Carlo process using standard methods. The random access memory available on typical engineering workstations will accomodate a voxel array large enough to make errors due to lack of spatial resolution negligible.

The maximum value in the voxel array is calculated and one-half this value subtracted from every value in the array. The surface of the object will thereby correspond to the locus of voxels with values near zero.

The spatial coordinates of each voxel with respect to the computed tomographic coordinate system being known, these are transformed to coordinates with respect to the system set up in the Monte Carlo code. The necessary transformations will be obvious to those practiced in the art. Every point in the Monte Carlo system is thereby associated with a number, where positive numbers correspond to the interior of the object and negative numbers to empty space.

The required distance from the given point to the surface along the ray direction is computed in the HOWFAR subroutine as follows. Assuming a distance along the ray from the initial point, the coordinates of the endpoint can be calculated, and corresponding voxel value determined. It is necessary to determine at what distance the voxel values change from positive to negative.

This can be accomplished using the standard bisection method which is robust and well-known to the art. The initial distances which are assumed are a series of increasing steps. When the voxel value returns negative, the distance is stepped halfway back to the last distance, and then backwards or forwards halfway to the next, and so forth. This process quickly converges to find the required distance. The distance value is then returned by the HOWFAR subroutine as required. Other numerical methods besides bisection technique can accomplish the same result and are known to those skilled in the art.

By this means, the x-ray scatter produced by the object is automatically calculated for each projection view without the need to characterize the object geometry. These scatter calculations are used to correct the original projection view data. Using the corrected projection views, the computed tomographic system will reconstruct a corrected three-dimensional image in the manner previously described.

Having thus set forth the nature of the invention, what is claimed is:

1. A method for correcting errors in the three-dimensional image of an object as measured by a volumetric computed tomographic device wherein said errors are induced by the scattering of x-rays by the object, comprising:
   (a) configuring the EGS4 Monte Carlo Code System to simulate the overall geometry of the volumetric computed tomographic system, in particular the position and characteristics of the x-ray source and those of the planar projection view detector,
   (b) importing the uncorrected three-dimensional image array as provided by said computed tomographic system into the Monte Carlo process, (c) transforming the spatial coordinates of the image array from those of the computed tomographic system to those of said EGS4 Code System, (d) finding the maximum value of the image array and subtracting one-half this value from all elements of the array, (e) importing an uncorrected projection view as provided by the computed tomographic device into the Monte Carlo process, (f) translating and rotating as required the spatial coordinates of the three-dimensional image array so as to correspond to the particular projection view, (g) running the EGS4 Monte Carlo Code System and computing in the subroutine HOWFAR the distance from a given point along a given direction to the point where the image array values change sign by using the bisection or equivalent method, (h) counting the total number of simulated x-rays at the end of the Monte Carlo run reaching each pixel in the simulated projection plane and the number of these scattered by the target, (i) transforming the x-ray counts into energy units and calculating the fraction of energy induced by scattered x-rays at every pixel in the simulated projection view, (j) subtracting the calculated fraction of scattered energy from the measured signal at every pixel in the uncorrected projection view, (k) returning the corrected projection view to the computed tomographic system, (l) repeating steps (e) through (k) for every uncorrected projection view as measured by the computed tomographic system, whereby said volumetric computed tomographic system will provide a corrected three-dimensional image of the object.

* * * * *